United States Patent [19]

Hennessy

[11] 4,020,111
[45] Apr. 26, 1977

[54] PROPYNYLOXY ALKYL ARENE INSECTICIDES

[76] Inventor: Douglas J. Hennessy, 47 Grayson Place, Teaneck, N.J. 07666

[22] Filed: May 28, 1975

[21] Appl. No.: 581,536

Related U.S. Application Data

[62] Division of Ser. No. 397,127, Sept. 13, 1973, abandoned, which is a division of Ser. No. 164,411, July 20, 1971, abandoned.

[52] U.S. Cl. .................. 260/611 A; 260/566 AE; 260/340.9; 260/310 C; 424/327; 424/274; 424/282; 424/339; 424/300; 424/198; 424/306
[51] Int. Cl.² ......................................... C07C 41/00
[58] Field of Search ............................. 260/611 A

[56] References Cited

UNITED STATES PATENTS

| | | | |
|---|---|---|---|
| 3,338,950 | 8/1967 | Seki et al. | 260/465 |
| 3,362,871 | 1/1968 | Fellig et al. | 260/612 D X |
| 3,839,562 | 10/1974 | Chodnekar et al. | 424/187 |
| 3,840,604 | 10/1974 | Chodnekar et al. | 260/613 D |

FOREIGN PATENTS OR APPLICATIONS 6,601,926  8/1966  Netherlands

OTHER PUBLICATIONS

Barnes et al., J. Econ. Entomol., vol. 62 (1969) pp. 86-89.
Schales et al., J.A.C.S. vol. 74 (1952) 4486-4490.
Sacher et al., J. Agr. Food Chem., vol. 16 (1968) 779-786.
Chem. Abstracts, vol. 57 (1962) 16451.
Hennessy, Biochemical Toxicology of Insecticides (1970) 105-114.
Metcalf, Ann. Rev. Entomol., vol. 12 (1967) 229-256.

*Primary Examiner*—Bernard Helfin
*Attorney, Agent, or Firm*—Davis, Hoxie, Faithfull & Hapgood

[57] ABSTRACT

Certain propynyl compounds, some of which are structurally novel, have been found to enhance the activity of carbamate, organophosphorus and chrysanthemum mono- and di-carboxylic ester insecticides.

7 Claims, No Drawings

PROPYNYLOXY ALKYL ARENE INSECTICIDES

This is a division of U.S. patent application Ser. No. 397,127, filed Sept. 13, 1973, which is a division of U.S. patent application Ser. No. 164,411, filed July 20, 1971, both now abandoned.

This invention relates to new propynyl compounds, to new synergistic insecticidal compositions comprising such compounds, and to their use.

It has been discovered that certain propynyl compounds, more fully described below, synergistically enhance the insecticidal activity of carbamate, organophosphorus and chrysanthemum mono- and di-carboxylic ester insecticides. This synergistic action is, moreover, highly selective in that the toxicity of the insecticides to warm-blooded animals is not appreciably increased.

The propynyl synergist compounds of the invention operate to protect the environment in which they are used by permitting the use of a lesser dose of insecticide to obtain a percentage insect mortality comparable to that which would result from a larger dose of insecticide alone. This is of particular importance where the insecticide is environmentally persistent or is highly toxic to birds, fish or mammals. Further, in a number of instances, these propynyl synergist compounds broaden the spectrum of activity of the insecticide. They also restore the activity of insecticides against insects which have developed resistance to the insecticide where such resistance is due to metabolism, i.e. enzymic detoxification, of the insecticide. In so restoring activity against resistant insects, it is believed that the propynyl synergist compounds act to inhibit enzymic detoxification.

The insecticidal carbamates with which the synergist compounds of this invention may be used include: 3,4-xylyl methyl carbamate; 3,4,5-trimethylphenyl methylcarbamate; 2,3,4-trimethylphenyl methylcarbamate; m-cym-5-yl-methylcarbamate; o-sec-butylphenyl methylcarbamate; m-(1-ethylpropyl) phenyl methylcarbamate; m-(1-methylbutyl) phenyl methylcarbamate; 3,4-di-t-butylphenyl methylcarbamate; o-chlorophenyl methylcarbamate; o-isopropoxyphenyl methylcarbamate [Baygon]; 4-(methylthio) 3,4-xylyl methylcarbamate; 4-dimethylamino-m-tolyl methylcarbamate; 4-dimethylamino-3,5-xylyl methylcarbamate; m-{[(dimethylamino)methylene]amino} phenyl methylcarbamate, hydrochloride; o-(1,3-dioxolan-2-yl) phenyl methylcarbamate; o-(4,5-dimethyl-1,3-dioxolan-2-yl) phenyl methylcarbamate; 1-naphthyl methylcarbamate [carbaryl]; 2,3-dihydro-2,2-dimethyl-7-benzofuranyl methylcarbamate; 1-(dimethylcarbamoyl)-5-methyl-3-pyrazolyl dimethylcarbamate [Dimetilan]; 3-methyl-1-phenyl-5-pyrazolyl-N-dimethylcarbamate [pyrolan]; 4-benzo(b) thienyl-N-methylcarbamate [mobam]; 8-(2-methylquinolyl)-N-methylcarbamate [GS 13798]; and 3,5-di-isopropylphenyl methylcarbamate [HRS 1422]. The preferred insecticidal carbamates are carbaryl, mobam, pyrolan, Dimetilan, Baygon, GS 13798 and HRS 1422.

The insecticidal organophosphorus compounds with which the synergist compounds of the invention may be used include: 3-hydroxy-N,N-dimethyl-cis-crotonamide, dimethyl phosphate [Bidrin]; 2-chloro-N,N-diethyl-3-hydroxycrotonamide, dimethyl phosphate; O,O-dimethyl S(4-oxo-1,2,3-benzotriazin-3 (4H)-ylmethyl) phosphorodithioate; 2-chloro-1-(2,4-dichlorophenyl) vinyl diethyl phosphate; 2-chloro-1-(2,4,5-trichlorophenyl) vinyl dimethyl phosphate [Gardona]; S-((2-methoxy-5-oxo-Δ$^2$-1,3,4-thiadiazolin-4-yl)methyl) O,O-dimethyl phosphorodithioate [GS 13005]; and O,O-diethyl O-(2-isopropyl-4-methyl-6-pyrimidyl) phosphorothioate [Diazinon]. The preferred insecticidal organophosphorus compounds are GS 13005, Diazinon, Gardona and Bidrin.

The synergist compounds of the present invention may be employed with insecticidal esters of 2,2-dimethyl-3-(2-methylpropenyl)-cyclopropanecarboxylic acid. The preferred esters are 3-(2,4-pentadienyl)-4-oxo-2-cyclopenten-1-yl chrysanthemumate, 3-(2-butenyl)-4-oxo-2-cyclopenten-1-yl-chrysanthemumate, 3-allyl-2-methyl-4-oxo-2-cyclopenten-1-yl chrysanthemumate, 6-chloropiperonyl chrysanthemumate, 2,4-dimethylbenzyl chrysanthemumate, 2,3,4,5-tetrahydrophthalimidomethyl chrysanthemumate and (5-benzyl-3-furyl) methyl chrysanthemumate. These synergist compounds may also be utilized with insecticidal esters of 2,2-dimethyl-3-(2-carbomethoxypropenyl)-cyclopropanecarboxylic acid. The preferred esters are methyl 3(2,4-pentadienyl)-4-oxo-2-cyclopenten-1-yl chrysanthemumdicarboxylate and methyl 3(2-butenyl)-4-oxo-2-cyclopenten-1-yl chrysanthemumdicarboxylate.

The propynyl synergist compounds with which the present invention is concerned are of four classes: [I] O-(2-propynyl) oximes; [II] Benzyl 2-propynyl ethers; [III] N-(2-propynyl) indazoles; and [IV] (2-propynyloxy) alkyl arenes.

The novel O-(2-propynyl) oximes of this invention are represented by the formula

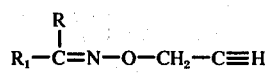  [I]

wherein the symbol R represents hydrogen, aryl or alkyl of not more than five carbon atoms; and where $R_1$ is (a) naphthyl, provided R is other than hydrogen, or (b) a substituted or unsubstituted aromatic hydrocarbon selected from the group consisting of

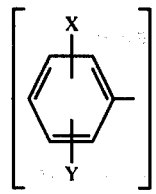

wherein X and Y represent hydrogen, nitro, substituted amino, alkoxy of less than three carbon atoms, or, when R is other than hydrogen, halogen other than iodine.

Examples of these oximes are given in Table I.

TABLE I

| Compound No. | R | $R_1$ |
|---|---|---|
| I-A | H | $(3,4-(CH_3O)_2)C_6H_3-$ |
| I-B | H | $(3-NO_2)C_6H_4-$ |
| I-C | H | $(4-(CH_3)_2N)C_6H_3-$ |
| I-D | $CH_3$ | $(4-Cl)C_6H_4-$ |
| I-E | $CH_3$ | $C_6H_5-$ |
| I-F | $CH_3$ | $\beta-C_{10}H_7-$ |

As illustrated in Example 5, the oximes of formula I synergistically enhance the lethality of insecticidal carbamates.

It has been found that the lethality of insecticidal organophosphorus compounds and of the aforesaid insecticidal cyclopropanecarboxylic acid esters is synergistically enhanced by 0-(2-propynyl) oximes represented by the formula

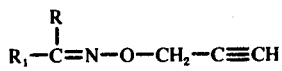
[Ia]

wherein R represents hydrogen, aryl, or alkyl of not more than five carbon atoms and $R_1$ represents a substituted or unsubstituted aromatic hydrocarbon group selected from the class consisting of naphthyl and groups having the structure

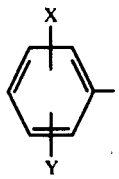

where X and Y represent hydrogen, nitro or halogen other than iodine.

Examples of these oximes are compounds I-B, I-D, I-E, I-F and the compounds of Table Ia.

TABLE Ia

| Compound No. | R | $R_1$ |
|---|---|---|
| I-G | H | $(2,4-Cl_2)C_6H_3-$ |
| I-H | H | $(4-Cl)C_6H_4-$ |
| I-I | H | $\alpha-C_{10}H_7-$ |

The lethality of insecticidal carbamates has been found to be enhanced synergistically by benzyl 2-propynyl ethers represented by the formula

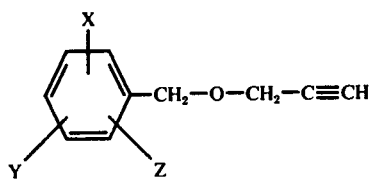
[II]

wherein X, Y and Z represent hydrogen, nitro, halogen other than iodine, or, when X is hydrogen, Y and Z taken together may represent methylenedioxy, and provided that, when both X and Y are hydrogen, Z is other than nitro.

Examples of these benzyl 2-propynyl ethers are given in Table II and their synergistic activity with insecticidal carbamates is illustrated in Example 6.

TABLE II

| Compound No. | X | Y | Z |
|---|---|---|---|
| II-A | H | H | 4—Cl |
| II-B | H | 2—Cl | 4—Cl |
| II-C | H | 3—Cl | 4—Cl |
| II-D | 2—Cl | 3—Cl | 4—Cl |
| II-E | 2—Cl | 3—Cl | 6—Cl |
| II-F | 2—Cl | 4—Cl | 5—Cl |
| II-G | H | 3,4—CH$_2$O$_2$ | |
| II-H | H | 2—Cl | 6—Cl |

TABLE II-continued

| Compound No. | X | Y | Z |
|---|---|---|---|
| II-I | H | 2—NO$_2$ | 3—Cl |
| II-J | H | 2—NO$_2$ | 4—Cl |
| II-K | H | 2—NO$_2$ | 6—Cl |
| II-L | H | 3—NO$_2$ | 2—Cl |
| II-M | H | 3—NO$_2$ | 4—Cl |
| II-N | H | 4—NO$_2$ | 2—Cl |
| II-O | H | 4—NO$_2$ | 3—Cl |

It has been found that the lethality of insecticidal organophosphorus compounds and of the aforesaid cyclopropanecarboxylic acid esters is synergistically enhanced by benzyl 2-propynyl ethers represented by the formula

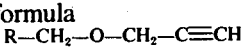

wherein R represents an aromatic hydrocarbon selected from the class consisting of naphthyl and groups having the structural formula

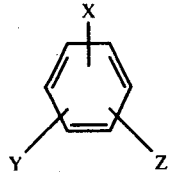

wherein X, Y and Z represent hydrogen, nitro or halogen other than iodine.

Examples of these benzyl 2-propynyl ethers are compounds II-A through II-F and II-H through II-O, inclusive, and the compounds of Table IIa.

TABLE IIa

| Compound No. | R |
|---|---|
| II-P | $(2-NO_2)C_6H_4-$ |
| II-Q | $(4-NO_2)C_6H_4-$ |
| II-R | $\alpha-C_{10}H_7-$ |

The novel N-(2-propynyl) indazoles of this invention are represented by the formula

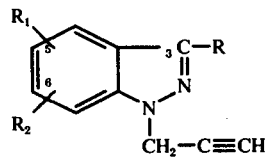
[III]

wherein R represents hydrogen or halogen other than iodine, $R_1$ represents hydrogen or nitro, and $R_2$ represents hydrogen, nitro or halogen other than iodine.

Examples of these indazoles are given in Table III and their synergistic activity with insecticidal carbamates is illustrated in Example 7.

TABLE III

| Compound No. | R | $R_1$ | $R_2$ |
|---|---|---|---|
| III-A | H | H | 5—NO$_2$ |
| III-B | 3—Cl | H | H |
| III-C | 3—Cl | H | 6—NO$_2$ |
| III-D | H | H | 6—Cl |

The novel (2-propynyloxy) alkyl arenes of this invention are represented by the formula

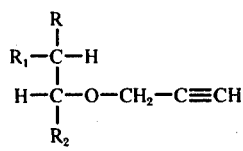

wherein R represents hydrogen or alkyl of not more than three carbon atoms, $R_1$ represents nitro, chlorine or bromine, and $R_2$ represents an aromatic hydrocarbon selected from the class consisting of naphthyl and groups having the formula

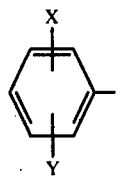

wherein X and Y represent hydrogen, nitro or halogen other than iodine.

Examples of these compounds are given in Table IV and their synergistic activity with insecticidal carbamates and insecticidal organophosphorus compounds is illustrated in Examples 8 and 11, respectively.

TABLE IV

| Compound No. | R | $R_1$ | $R_2$ |
|---|---|---|---|
| IV-A | $CH_3$ | $NO_2$ | $(2,4-Cl_2)C_6H_3-$ |
| IV-B | $CH_3$ | $NO_2$ | $\alpha-C_{10}H_7-$ |
| IV-C | $CH_3$ | $NO_2$ | $(4-Cl)C_6H_4-$ |

The following examples illustrate the preparation of propynyl compounds within the foregoing four classes.

EXAMPLE 1

Preparation of O-(2-propynyl) Oximes.

Oximes (R $R_1$ C NOH) having the R and $R_1$ substituents identified in Tables I and Ia were first prepared from commercially available aldehydes or ketones by the method of Shriner, Fuson and Curtin (1). A mixture of 10 g of hydroxylamine hydrochloride was dissolved in 200 ml of 10% sodium hydroxide solution. If the aldehyde was water insoluble, sufficient 95% ethanol was added to the reaction mixture to form a clear solution. The mixture was warmed on the steam bath for 6 hours, and then acidified with concentrated hydrochloric acid. The precipitate was collected by suction filtration and recrystallized from dilute ethanol to give the desired oximes. The oximes were found to have the syn configuration. The O-(2-propynyl) oximes were then prepared by the following modification of the procedure of Smith and Robertson (2). To a solution of sodium ethoxide prepared from 0.23 g (0.10 mol) of sodium metal and 100 ml of absolute ethanol, the oxime was added. To the stirred solution was added 1.18 g (0.10 mol) of propynyl bromide, and the reaction mixture was stirred at room temperature until sodium bromide precipitated, and then refluxed for an additional hour. If after 3 hours of stirring at room temperature, sodium bromide did not precipitate, then the reaction mixture was refluxed until sodium bromide did precipitate. The reaction mixture was poured into 100 ml of water, and the oily layer was extracted with ether. The ether layer was separated, washed with water, 10% potassium hydroxide solution, saturated sodium chloride solution, dried ($Na_2SO_4$) and concentrated in vacuo. The residue was either recrystallized from 95% ethanol or distilled under vacuum to give the O-(2-propynyl) oxime.

1. R. L. Shriner, R. C. Fuson, and D. Y. Curtin, "The Systematic Identification of Organic Compounds", 5th ed., John Wiley and Sons, New York, N.Y. (1965). The disclosure of Shriner, et al., and of all other footnoted references, are incorporated herein in full by reference thereto.
2. P. Smith and J. E. Robertson, J. Amer. Chem. Soc., 84, 1197 (1962).

The yields, melting points, analyses and spectral data are given in Tables V and Va.

TABLE V

| Compound No. | Yield % | Mp, °C | Analyses % Calcd. | Found | Ir, $cm^{-1}$ (assignment) | Nmr, $\delta$, ppm. (assignment) |
|---|---|---|---|---|---|---|
| I-A | 77 | 61 | C 65.74<br>H 5.98<br>N 6.39 | 65.97<br>6.23<br>6.23 | 3279 (C≡C—H)<br>2123 (C≡C)<br>1047 (C—O)<br>1010 (N—O) | H<br>8.00 (s,1,C=N)<br>7.25 (d,1,J=2Hz,$H_2$)<br>7.00 (dd,1,J=8Hz,J=2Hz,$H_6$)<br>6.76 (d,1,J=8Hz,$H_5$)<br>4.69 (d,2,J=2Hz,O—$CH_2$)<br>3.84 (s,3,O—$CH_3$)<br>3.82 (s,3,O—$CH_3$)<br>2.32 (t,1,J=2Hz,C≡C—H) |
| I-B | 50 | 74-5 | C 58.82<br>H 5.87<br>N 13.72 | 58.92<br>5.58<br>13.91 | 3342 (C≡C—H)<br>2119 (C≡C)<br>1522,1351 ($NO_2$)<br>1047 (C—O)<br>1010 (N—O) | 8.54 (m,1,$H_2$)<br><br>8.15 (s,1,C=N)<br>8.25 (d,1,J=8Hz,fine splitting,$H_6$)<br>8.02 (d,1,J=8Hz,fine splitting,$H_5$)<br>7.70 (d,1,J=9Hz,$H_4$)<br>4.79 (d,2,J=2Hz,O—$CH_2$)<br>2.37 (t,1,J=2Hz,C≡C—H) |
| I-C | 32 | 74 | C 71.24<br>H 6.98<br>N 13.86 | 71.25<br>7.04<br>13.85 | 3322 (C≡C—H)<br>2119 (C≡C)<br>1053 (C—O)<br>1010 (N—O) | H<br>7.85 (s,1,C=N)<br>7.36 (d,2,J=8Hz,Ar—H)<br>6.54 (d,2,J=8Hz,Ar—H)<br>4.60 (d,2,J=2Hz,O—$CH_2$)<br>2.92 (s,6,N—$CH_3)_2$<br>2.27 (t,1,J=2Hz,C≡C—H) |
| I-D | 81 | 48 | C 63.41<br>H 5.14 | 53.13<br>5.26 | 3344 (C≡C—H)<br>2119 (C≡C) | 8.67 (d,2,J=8Hz,Ar—H)<br>7.23 (d,2,J=8Hz,Ar—H) |

-continued

| | | | | | | Ir, cm$^{-1}$ | Nmr, δ,ppm. |
|---|---|---|---|---|---|---|---|
| | | | | | | 1052 (C—O) | 4.65 (d,2,J=2Hz,O—CH$_2$) |
| | | | | | | 1009 (N—O) | 2.32 (t,1,J=2Hz,C≡C—H) |
| | | | | | | | 2.19 (s,3,CH$_3$) |
| I-E | 50 | 59–60 | C 81.68 | 80.97 | 3333 (C≡C—H) | | 7.69 (m,10,Ar—H) |
| | | | H 5.57 | 5.74 | 1054 (C—O) | | 4.73 (d,2,J=2Hz,O—CH$_2$) |
| | | | N 5.97 | 5.95 | 1010 (N—O) | | 2.38 (t,1,J=2Hz,C≡C—H) |
| I-F | 49 | 76–7 | C 80.69 | 80.43 | 3344 (C≡C—H) | | 7.81 (m,7,Ar—H) |
| | | | H 5.87 | 5.58 | 2123 (C—C) | | 4.85 (d,2,J=2Hz,O—CH$_2$) |
| | | | N 6.28 | 6.12 | 1047 (C—O) | | 2.32 (m,4,CH$_3$ and C≡C—H) |
| | | | | | 1010 (N—O) | | |

TABLE Va

| Compound No. | R | R$_1$ | Yield % | Mp, °C | Analyses % Calcd. | Found | Ir, cm$^{-1}$ (assignment) | Nmr, δ,ppm. (assignment) |
|---|---|---|---|---|---|---|---|---|
| I-G | H | 2,4-Cl$_2$C$_6$H$_3$ | 45 | 67 | C 55.95 | 55.88 | 3236 (C≡C—H) | $\overset{H}{8.30}$ (s,1,C=N) |
| | | | | | H 3.28 | 3.36 | 2105 (C≡C) | 7.81 (d,1,J=8Hz,H$_6$) |
| | | | | | | | 1053 (C—O) | 7.32 (d,1,J=2Hz,H$_3$) |
| | | | | | | | 1008 (N—O) | 7.15 (dd,1,J=2Hz,J=8Hz,H$_5$) |
| | | | | | | | | 4.72 (d,2,J=2Hz,O—CH$_2$) |
| | | | | | | | | 2.34 (t,1,J=2Hz,C≡C—H) |
| I-H | H | 4-ClC$_6$H$_4$ | 41 | 65 | C 62.03 | 62.26 | 3333 (C≡C—H) | $\overset{H}{8.18}$ (s,1,C=N) |
| | | | | | H 4.16 | 4.19 | 1053 (C—O) | 7.51 (dd,2,J=6Hz,J=2Hz,Ar—H) |
| | | | | | N 7.23 | 7.31 | 1019 (N—O) | 7.31 (dd,2,J=6Hz,J=2Hz,Ar—H) |
| | | | | | | | | 4.76 (d,2,J=2Hz,O—CH$_2$) |
| | | | | | | | | 2.51 (t,1,J=2Hz,C≡C—H) |
| I-I | H | α-C$_{10}$H$_7$ | 77 | 58 | C 80.36 | 80.28 | 3268 (C≡C—H) | 8.59 (m,2,H$_9$ and C=N) |
| | | | | | H 5.30 | 5.44 | 2114 (C≡C) | 7.62 (m,6,Ar—H) |
| | | | | | | | 1052 (C—O) | 4.83 (d,2,J=2Hz,O—CH$_2$) |
| | | | | | | | 1003 (N—O) | 2.48 (t,1,J=2Hz,C≡C—H) |

EXAMPLE 2

Compounds II-A through II-F were prepared by following the general procedures of Guermont (3) and of Marszak, Diament and Guermont (4). To a stirred solution of 0.23 g (0.10 mol) of sodium metal dissolved in 90 ml of propynyl alcohol was added 0.01 mol of the appropriate benzyl halide. The reaction mixture was stirred at room temperature for three hours and then refluxed for one hour to insure completion of the reaction. The reaction mixture was poured into 100 ml of water, and the oily layer was extracted into ether. The ether layer was separated, washed with water, 10% sodium hydroxide solution, saturated sodium chloride solution, dried (Na$_2$SO$_4$) and concentrated in vacuo. Compounds II-A, II-B and II-C were distilled at reduced pressure, and compounds II-D and II-E and II-F were crystallized from 95% ethanol. Compound II-H may be similarly prepared using the appropriate benzyl halide.

3. J. P. Guermont, Mem. ser. chim. e'tat (Paris), 147 (1955). 4. I. Marszak, G. Diament and J. P. Guermont, Mem. ser. chim. e'tat (Paris) 35, 67 (1950).

Compound II-R was similarly prepared but was chromatographed on silica gel with benzene as the eluant.

Compounds II-P and II-Q were prepared in the following manner. A mixture of 1.38 g (0.01 mol) of anhydrous potassium carbonate, 0.01 mol of the appropriate benzyl halide and 1.38 g of propynyl alcohol dissolved in 100 ml of acetone was refluxed with stirring for 24 hours. The reaction mixture was poured into 100 ml of water, and the oily layer was extracted with ether. The ether layer was separated, washed with water, 10% sodium hydroxide solution, saturated sodium chloride solution, dried (Na$_2$SO$_4$) and concentrated in vacuo. Compound II-P was distilled at reduced pressure; II-Q was crystallized from 95% ethanol.

Compound II-G was prepared by a modification of the procedure employed in preparing compounds II-P and II-Q. 3,4-Methylenedioxybenzyl alcohol was substituted for propynyl alcohol, and propynyl bromide was substituted for the benzyl halide. The crude oil of II-G was dissolved hot in hexane, and upon cooling, the starting material, methylenedioxybenzyl alcohol precipitated. The solution was filtered, and the filtrate was concentrated in vacuo. The residue was chromatographed on an alumina column and eluted with benzene.

The 2-propynyl chloronitrobenzyl ethers, compounds II-I through II-O, inclusive, were prepared as follows. A solution of 5% (w/v) sodium propynylate in propynyl alcohol was prepared by reacting sodium metal or sodium hydride with anhydrous propynyl alcohol. To 170 ml of the sodium propynylate/propynyl alcohol there was added 0.1 mol of the chloronitrobenzyl bromide or chloronitrobenzyl chloride and the mixture was stirred at room temperature for 5 hours and then refluxed until essentially free of benzyl halide (1–2 hrs.). The major portion of the propynyl alcohol was removed by distillation under reduced pressure and the residue was treated with 100 ml of water and extracted with ether or benzene. The organic layer was separated, washed with saturated sodium chloride, dried (Na$_2$SO$_4$) and fractionally distilled in vacuo to collect the respective chloronitrobenzyl 2-propynyl ether which was identified by infrared and nuclear magnetic resonance spectra.

The yields, melting or boiling points, analyses and spectral data are given in Tables VI and VIa.

TABLE VI

| Compound | Yield | Bp.(mm) or | Analyses % | Ir, cm$^{-1}$ | Nmr data, δ, ppm. |
|---|---|---|---|---|---|

-continued

| No. | % | mp, °C | Calcd. | Found | Ir,cm⁻¹ (assignment) | Nmr data, δ, ppm. (assignment) |
|---|---|---|---|---|---|---|
| II-A | 60 | 63–5 (0.05) | | | 3322 (C≡C—H)<br>2381 (C≡C) | 6.96 (s,4,Ar—H)<br>4.33 (s,2,Ar—CH₂)<br>3.86 (d,2,J=2Hz,CH₂—≡C—H)<br>2.19 (t,i,J=2Hz,C≡C—H) |
| II-B | 90 | 76–81 (0.05) | C 55.84<br>H 3.75 | 55.92<br>3.83 | 3279 (C≡C—H)<br>2114 (C≡C) | 7.11 (m,3,Ar—H)<br>4.40 (s,2,Ar—CH₂)<br>4.08 (d,2,J=2Hz,CH₂—C≡C—H)<br>2.38 (t,1,J=2Hz,C≡C—H) |
| II-C | 75 | 79–81 (0.07) | C 55.84<br>H 3.75 | 55.71<br>3.83 | 3322 (C≡C—H)<br>2123 (C≡C) | 7.20 (m,3,Ar—H)<br>4.48 (s,2,Ar—CH₂)<br>4.12 (d,2,J=2Hz,CH₂—C≡C—H)<br>2.35 (t,1,J=2Hz,C≡C—H) |
| II-D | 85 | 57 | C 48.14<br>H 2.83 | 48.11<br>2.75 | 3222 (C≡C—H)<br>2171 (C≡C) | 7.31 (s,2,Ar—H)<br>4.58 (s,2,Ar—CH₂)<br>4.19 (d,2,J=2Hz,CH₂—C≡C—H)<br>2.28 (t,1,J=2Hz,C≡C—H) |
| II-E | 95 | 29 | C 48.14<br>H 2.83 | 48.24<br>2.85 | 3311 (C≡C—H)<br>2228 (C≡C) | 7.49 (d,1,J=8Hz,Ar—H)<br>7.26 (d,1,J=8Hz,Ar—H)<br>4.86 (s,2,Ar—CH₂)<br>4.23 (d,2,J=2Hz,O—CH₂)<br>2.44 (t,1,J=2Hz,C≡C—H) |
| II-F | 50 | 35 | C 48.14<br>H 2.83 | 48.02<br>2.97 | 3279 (C≡C—H)<br>2279 (C≡C) | 7.50 (s,1,Ar—H)<br>7.35 (s,1,Ar—H)<br>4.53 (s,2,Ar—CH₂)<br>4.23 (d,2,J=2Hz,CH₂—C≡C—H)<br>2.36 (t,1,J=2Hz,C≡C—H) |
| II-G | 20 | | C 69.46<br>H 5.30 | 69.98<br>5.53 | 3268 (C≡C—H)<br>2123 (C≡C) | 6.87 (m,3,Ar—H)<br>6.03 (s,2,O—CH₂—O)<br>4.53 (s,2,Ar—CH₂)<br>4.14 (d,2,J=2Hz,O—CH₂)<br>2.37 (t,1,J=2Hz,C≡C—H) |

TABLE VIa

| Compound No. | Compound Name and Formula | Yield % | Bp. (mm) or Mp, °C | Analyses % Calcd. | Found | Ir,cm⁻¹ (assignment) | Nmr data, δ, ppm. (assignment) |
|---|---|---|---|---|---|---|---|
| II-P | 2-nitrobenzyl 2-propynyl ether<br>2-NO₂C₆H₄CH₂—<br>—O—CH₂C≡CH | 30 | 95 (0.05) | C 62.82<br>H 4.74<br>N 7.33 | 62.77<br>4.81<br>7.37 | 3279 (C≡C—H)<br>2281 (C≡C)<br>1650,1333 (NO₂) | 7.55 (m,4,Ar—H)<br>4.73 (s,2,Ar—CH₂)<br>4.08 (d,2,J=2Hz,CH₂—C≡C—H)<br>2.23 (t,1,J=2Hz,C≡C—H) |
| II-Q | 4-nitrobenzyl 2-propynyl ether<br>4-NO₂C₆H₄—CH₂—<br>—O—CH₂—C≡CH | 20 | 57 | C 62.82<br>H 4.74<br>N 7.33 | 62.89<br>4.74<br>7.31 | 3279 (C≡C—H)<br>2119 (C≡C)<br>1522,1351 (NO₂) | 7.64 (d,2,J=8Hz,Ar—H)<br>7.00 (d,2,J=8Hz,Ar—H)<br>4.21 (s,2,Ar—CH₂)<br>3.71 (d,2,J=2Hz,CH₂—C≡C—H)<br>1.97 (t,1,J=2Hz,C≡C—H) |
| II-R | α-naphthylmethyl 2-propynyl ether<br>α-C₁₀H₇—CH₂—<br>—O—CH₂—C≡CH | 40 | | C 85.68<br>H 6.16 | 85.93<br>6.24 | 3250 (C≡C—H)<br>2265 (C≡C) | 8.06 (m,1,peri H)<br>7.55 (m,7,Ar—H)<br>4.95 (d,2,Ar—CH₂)<br>4.07 (d,2,J=2Hz,O—CH₂)<br>2.34 (t,1,J=2Hz,C≡C—H) |

EXAMPLE 3

Preparation of N-(2-propynyl) Indazoles

Compounds III-A, III-B and III-D were prepared by a modification of the procedure of Zaugg, Swett and Stone (5). In a stirred solution of sodium ethylate prepared from 0.23 g (0.01 mol) of sodium metal and 50 ml of absolute ethanol was dissolved 0.01 mol of the appropriate nitro- or chloroindazole. To such solution was added 2.38 g (0.02 mol) of propynyl bromide, and the reaction mixture was stirred for 24 hours at room temperature during which time sodium bromide precipitated. The reaction mixture was poured into 100 ml of water and the oily layer was extracted with ether.

The ether layer was separated, washed with water, 10% potassium hydroxide solution, saturated sodium chloride solution, dried ($Na_2SO_4$) and concentrated in vacuo. The residue was recrystallized from 95% ethanol to give the desired N-(2-propynyl) indazoles. To prepare compound III-C, a mixture of 10 g (0.043 mol) of 3-chloro-6-nitroindazole, 6.9 g (0.043 mol) of anhydrous potassium carbonate and 0.10 g (0.086 mol) of propynyl bromide was placed in 100 ml of acetone. The reaction mixture was refluxed for 24 hours, and then poured into 100 ml of water. The oil layer was extracted with ether, and the ether layer was separated, washed with water, 10% sodium hydroxide solution, saturated sodium chloride solution, dried ($Na_2SO_4$) and concentrated in vacuo. The residue was recrystallized from 95% ethanol to give N-(2-propynyl)-3-chloro-6-nitroindazole.

5. H. E. Zaugg, L. R. Swett, and G. R. Stone, *J. Org. Chem.* 23, 1389 (1958)

The yields, melting points, analyses and spectral data are given in Table VII.

10.08 (s,broad,1,Ar-CH=C), 7.35 (m,7,Ar-H), and 3.93 ppm (s,broad,3,$CH_3$).

Anal. Calcd. for $C_{13}H_{11}NO_2$: C, 73.23; H, 5.20; N, 6.57. Found: C, 73.07; H, 5.39; N, 6.27.

To prepare 2-propynyl 1-(2,4-dichlorophenyl)-2-nitropropyl ether, 50 ml of anhydrous ether was added to a solution of sodium propynylate prepared from 0.8 g (0.035 mol) of sodium metal and 50 ml of propynyl alcohol. The above mixture was cooled in an ice bath, and 5 g (0.023 mol) of 1-(2,4-dichlorophenyl)-2-nitropropene was added. The reaction mixture was stirred at room temperature for one hour and then refluxed for an additional hour. The reaction mixture was poured into water, and the solution was extracted with ether. The water layer was separated and slowly acidified with glacial acetic acid, while keeping the temperature between 0° C and 5° C. The oily layer was extracted with ether, washed with saturated sodium bicarbonate, saturated sodium chloride solution, dried ($Na_2SO_4$) and concentrated in vacuo. The residue was chromato-

TABLE VII

| Compound No. | Yield % | Mp, °C | Analyses % Calcd. | Analyses % Found | Ir,cm$^{-1}$ (Assignment) | Nmr, δ,ppm (Assignment) |
|---|---|---|---|---|---|---|
| III-A | 50 | 94 | C 59.70 | 59.70 | 3381 (C≡C—H) | 7.81 (s,1,$H_3$) |
|  |  |  | H 3.51 | 3.48 | 2119 (C≡C) | 7.37 (dd,1,J=9Hz,$H_6$) |
|  |  |  | N 20.89 | 20.86 | 1520,1137 ($NO_2$) | 7.22 (d,1,J=2Hz,$H_4$) |
|  |  |  |  |  |  | 7.07 (d,1,J=9Hz,$H_7$) |
|  |  |  |  |  |  | 4.48 (d,2,J=2Hz,N—$CH_2$) |
| III-B | 64 | 85 | C 63.01 | 62.85 | 3300 (C≡C—H) | 1.64 (t,1,J=2Hz,C≡C—H) |
|  |  |  | H 3.70 | 3.91 | 2151 (C≡C) | 8.11 (m,4,Ar—H) |
|  |  |  |  |  |  | 5.05 (d,2,J=2Hz,N—$CH_2$) |
| III-C | 47 | 124 | C 50.94 | 50.86 | 3247 (C≡C—H) | 2.39 (t,1,J=2Hz,C≡C—H) |
|  |  |  | H 2.57 | 2.61 | 2117 (C≡C) | 8.86 (d,1,J=2Hz,$H_7$) |
|  |  |  |  |  | 1517,1335 ($NO_2$) | 8.10 (dd,1,J=2Hz,J=9Hz,$H_5$) |
|  |  |  |  |  |  | 7.79 (d,1,J=9Hz,$H_4$) |
|  |  |  |  |  |  | 5.21 (d,2,J=2Hz,N—C-$H_2$) |
| III-D | 52 | 112 | C 63.01 | 63.21 | 3247 (C≡C—H) | 2.48 (t,1,J=2Hz,C≡C—H) |
|  |  |  | H 3.70 | 3.93 | 2128 (C≡C) | 7.91 (s,1,$H_3$) |
|  |  |  | N 14.70 | 14.67 |  | 7.77 (d,1,J=2Hz,$H_7$) |
|  |  |  |  |  |  | 7.60 (d,1,J=9Hz,$H_4$) |
|  |  |  |  |  |  | 7.35 (dd,1,J=9Hz,J=2Hz,$H_5$) |
|  |  |  |  |  |  | 5.17 (d,2,J=2Hz,N—$CH_2$) |
|  |  |  |  |  |  | 2.31 (t,1,J=2Hz,C≡C—H) |

EXAMPLE 4

Preparation of (2-propynyloxy) Alkyl Arenes.

Exemplary of the preparation of these compounds is the preparation of 2-propynyl 1-aryl-2-nitropropyl ethers, such as compounds IV-A and IV-B, by the Michael-type addition of sodium propynylate to the double bond of the appropriate 1-aryl-2-nitropropene (6)(7).

6. M. Koremura, H. Oku, T. Shono, and T. Nakanishi, *Jakamine Kenkyusho Nempo*, 13, 198 (1961); Chem. Abstr. 57, 16451 (1962).
7. P. Schales and E. Grafe, *J. Amer. Chem. Soc.*, 74, 4489 (1952).

hours. The reaction mixture was poured onto 100 g of ice, and the oily layer was extracted with benzene. The benzene layer was separated, washed with saturated sodium bisulfate, saturated sodium chloride, dried ($Na_2SO_4$), and concentrated in vacuo.

The unreacted naphthaldehyde was removed under reduced pressure, (0.03 mm). The pot residue was recrystallized from 95% ethanol to give 8.5 g (33%) of 1-naphthyl-2-nitro-propene mp 64°–7°; ir (KBr) 1639 (C=C), 1522 and 1311 cm$^{-1}$ ($NO_2$); nmr ($CCl_4$) δ graphed on 30 g of silica gel and eluted with benzene to give a yield of 2.55 g (37%) ir ($CCl_4$) 3268 (C C—H), and 1558 cm$^{-1}$ (unconj. ($NO_2$); nmr ($CCl_4$) δ 7.40 (m,3,Ar—H) 5.71 (d,1,J=3Hz,Ar-CH), 5.54 (d,1,J=9Hz,Ar-CH), 4.69 (m,1,CH-$NO_2$), 4.05 (m,2,O-$CH_2$), 2.36 (m,1,C≡C-H), 1.41 (d,3,J=Hz,$CH_3$) and 1.33 ppm (d,3,J=8Hz,$CH_3$).

Anal. Calcd. for $C_{12}H_{10}Cl_2NO_3$: C, 50.02; H, 3.85; N, 4.86. Found: C, 50.07; H, 3.83; N, 4.80

2-propynyl 1-naphthyl-2-nitropropyl ether was prepared by adding 50 ml of anhydrous ether and 5 g (0.023 mol) of 1-naphthyl-2-nitropropene to a solution of sodium propynylate prepared from 1 g (0.023 mol) of sodium metal and 50 ml of propynyl alcohol cooled in an ice bath. The reaction mixture was stirred at room temperature for one hour and refluxed for 3 hours. The reaction mixture was worked up as in the preparation of the 2,4-dichlorophenyl compound to give 3.08 g (50%) of crude 1-naphthyl compound. An analytical sample was prepared by chromatographing 1 g of the crude naphthyl compound on 20 g of silica gel and eluting with benzene. 2-propynyl 1-naphthyl-2-nitropropyl ether was then crystallized from absolute ethanol: mp 74°; ir (CCl$_4$)3331 (C≡C-H), 2128 (C≡C) and 1543 cm$^{-1}$ (unconj. NO$_2$); nmr (CCl$_4$) δ8.23 (m,1,peri H); 7.73 (m,6,Ar-H); 5.97 (d,1,J=4Hz,Ar-CH) 4.83 (m,1,CH-NO$_2$); 4.17 (m,2,O-CH$_2$), 2.17 (m,1,O≡C-H), and 1.48 ppm (d,3,J=7Hz, CH$_3$)

Anal. Calcd. for C$_{16}$H$_{15}$NO$_3$: C, 71.36; H, 5.61; N, 5.20. Found: 71.55; H, 5.70; N, 5.15.

In the foregoing examples, melting points were determined on a Fisher-Johns Apparatus. Melting points and boiling points were uncorrected. Infrared spectra were obtained on a Perkin-Elmer 137 Grating Spectrophotometer. Nuclear magnetic resonance spectra were determined on Varian A-60 and A-60A NMR Spectrophotometers, probe temperature 38°, with signals reported relative to internal tetramethylsilane. Nuclear magnetic resonance spectra and infrared spectra were taken in carbon tetrachloride. Thin layer chromatograms were carried out on Silica Gel G coated glass slides. Column chromatography was performed using Alumina Woelm, Neutral, activity I. Yields were based upon isolated product and no developmental work was performed to improve yields.

The effectiveness of the synergists disclosed herein is believed to be largely due to their ability to interfere with or inhibit the action of mixed function oxygenase (MFO), an entity present in insects, and which, in many cases at least, serves to metabolize insecticides to relatively innocuous products and hence to render them non-lethal. It follows that the synergistic effectiveness of any particular synergist with any particular insecticide depends not only on the efficacy of the synergist in inhibiting MFO metabolism, but the degree to which the particular insecticide is susceptible to detoxification by MFO metabolism.

Thus, for example, the insecticide carbaryl has a relatively low lethality to the common house fly by virtue of the ease with which it undergoes MFO metabolism to innocuous products in that insect. Synergists according to the invention are therefore very effective in terms of raising the lethality of carbaryl. On the other hand the insecticide Dimetilan is relatively lethal to house flies and while it can still be synergized to a significant extent by compounds according to the invention, the increase in lethality is less (and hence the degree of synergism is less) than with carbaryl.

In general, carbamate insecticides are synergized by compounds according to the invention to the extent that a combination of carbamate and insecticide will have the same lethality as a significantly greater dose of insecticide alone. This is generally true also of the insecticidal esters of chrysanthemum mono- and di-carboxylic acids.

The effect of synergist candidates administered jointly with organophosphorus (OP) insecticides in many cases brings about increased lethality. However, in some instances unchanged lethality or even decreased lethality is observed. According to the present state of knowledge, the observed decrease in lethality can be attributed, especially with some phosphorothioate or -dithioate insecticides, to the fact that at least some MFO metabolites of those insecticides are more lethal than the original compounds and the effectiveness of the original compounds as insecticides depends on MFO metabolism producing those lethal derivatives. By inhibiting or interfering with the MFO metabolism, it is postulated, the putative synergist may give a net effect in which inhibition of metabolic potentiation is of greater import than is inhibition of metabolic detoxification.

Where a net synergism is observed with OP insecticide, metabolic potentiation is either unimportant or is of less importance than metabolic detoxification. The lack of any effect by a synergist candidate can be explained either as a balancing of potentiation and detoxification, or as no significant inhibition of either type.

The following examples illustrate the enhanced lethality of insecticidal carbamates, insecticidal organophosphorus compounds and pyrethrum when utilized in conjunction with the above-described propynyl synergist compounds.

In the insecticidal compositions of the present invention comprising one of the aforementioned insecticidal compounds an one of the propynyl synergist compounds, from about 0.1 to about 10 parts by weight of the synergist compound may be employed per one part by weight of the insecticide compound. Preferably, there should be at least about 0.5 part by weight of synergist per one part by weight of insecticide.

The insecticidal compositions according to the invention may be used in a variety of ways and may be mixed with other materials such as vehicles, carriers and adjuvants whose nature will depend on the mode of application. Thus, for example, the active ingredients, insecticide and synergist, may be applied in a powder or dust in which case they may be mixed with a solid carrier such as a clay, for example, Fuller's earth, bentonite, talc, kieselguler or diatomaceous earth. Non-clay carriers such as by-product lignin, wood, and walnut shell flour may also be used.

For liquid spray application the active ingredients may be dispersed or dissolved in a liquid carrier. Various carriers known to the art may be employed including water, hydrocarbon solvents of various descriptions, lower ketones, alcohols and mixtures of such materials, provided that they are substantially inert to the active ingredients.

In some cases emulsions or dispersions of the active ingredients in the liquid carrier may be desirable and such may be prepared by agitation of the active ingredients with the carrier. Surface active emulsifying or dispersing agents may be employed to aid in the procedure, and in this connection there may be mentioned fatty alcohol sufates, for example, sulfonated castor oil or alkyl benzene sulfonates, soaps, such a sodium oleate and non-ionic surfactants such as high molecular weight alkyl polyglycol ethers. Such emulsifying and dispersing agents commonly possess wetting agent properties.

Compositions according to the invention may also contain adjuvants such as wettin agents and humectants.

In general, use compositions according to the invention (including the carrier and various adjuvants) may be formulated according to known techniques, and, in accordance with conventional practice, may contain from about 2 to about 20% by weight active ingredients (synergist and insecticide), though, of course, concentrates containing say 10–80% active ingredients may be prepared for sale with subsequent dilution by the user. It is contemplated that formulations according to the invention may be employed in aerosol dispensers, in which case the above proportions do not include the aerosol propellant. In aerosol uses the proportion of propellant to total charge will be that normally employed, for example, 25–95% of the total charge.

EXAMPLE 5

Synergism of Insecticidal Carbamates By O-(2-Propyny) Oximes.

The synergistic effect with carbaryl and pyrolan of the O-(2-propynyl) oximes identified in Table I was determined by the jar-film assay technique using unsexed, susceptible, three to five-day old, Wilson strain house flies that had not been subjected to selection by treatment with insecticide. The required solutions of the insecticide and of the synergist compound were prepared in acetone at a concentration of one milligram per milliliter. One-pint wide mouth glass jars were coated wiith the appropriate insecticide synergist combination by rolling the jars containing aliquots of the appropriate solutions diluted to three milliliters with acetone to deposit, by evaporation, a film of the test materials. The flies were transferred under carbon dioxide anesthesia and held in the jar at room temperature. Perforated aluminum foil was used to cover the jars and to hold cotton saturated with 10% sugar solution. Counts were made at intervals, but the recorded mortality was based on 24-hour kill, rather than knockdown. All prostrate nonmoving flies were considered dead. A determination was then made of the contact synergistic ratio [SR], which is the ratio of the $LC_{50}$ of insecticide alone to the $LC_{50}$ of the insecticide when applied together with the synergist. The $LC_{50}$ of the insecticide was estimated from a log-probit plot of percent kill versus dosage. The $LC_{50}$ of carbaryl alone for the Wilson strain fly is 1.0 mg/jar, by the jar-film assay tchnique; for pyrolan alone, the $LC_{50}$ is 0.15 mg/jar. The $LC_{50}$ of the combination of insecticide and synergist was determined at a synergist to insecticide parts by weight ratio of five to one. The results are shown in Table VIII.

TABLE VIII

| Compound No. | Contact Synergistic Ratio | |
| --- | --- | --- |
| | Carbaryl | Pyrolan |
| I-A | 200 | 30 |
| I-B | 270 | 35 |
| I-C | 200 | 20 |
| I-D | 177 | 25 |
| I-E | 100 | 10 |
| I-F | 200 | 50 | kills after 24 hours for the two tests were averaged and are shown in Table IX. These doses of insecticide used without synergist caused 10–40% mortality.

In Table IX, an in the tables following it, the doses of topically applied insecticides and of synergists unless otherwise noted are expressed as micrograms per fly ($\mu$g/fly).

TABLE IX

| | | Dimetilan | GS 13798 |
| --- | --- | --- | --- |
| Insecticide dose: | 0 | 2 | 1 |
| Synergist dose: | 10 | 4 | 2 |
| Synergist Compound No. | | | |
| I-A | 0 | 100 | 65 |
| I-D | 0 | 100 | 100 |
| I-F | 0 | 100 | 95 |

The synergistic effect of O-(2-propynyl) oximes with mobam was determined from topical application tests on susceptible, female, IN/WHO strain house flies and from tests on resistant, female, Rutgers A strain house flies. The synergist and insecticide were dissolved in ACS Grade acetone in such quantities that a 1.0$\mu$liter volume applied to the thorax of 3-to-5 day old $CO_2$-anesthetized female adult house flies contained the desired dosage. After being treated, the flies were confined, 10 to a plaster petri dish, with 3–5 dishes/treatment, and held for 24-hr. observation of mortality. Reconstituted skim milk on cotton dental wicks was provided during the holding period. The percent kills after 24 hours are shown in Table X for the IN/WHO strain and Table XI for the Rutgers A strain.

The mortality data of Table X for compound I-D illustrate the effect of doubling the dosages of insecticide both without and with the synergist at a synergist-insecticide ratio 5 to 1. when the dose of mobam alone was doubled from 0.05 mg/fly to 0.10 mg/fly, there was no increase in lethality. But, upon the same mobam dosage increase when in combination with the synergist, the percent mortality rose from 8 to 20%. Upon a further doubling of mobam dose, to 0.20 mg/fly, the percent mortality for the insecticide alone went from zero to 2%, but the increase in percent mortality for the mobam-synergist combination was from 20 to 92%.

The data of Table X for compound I-B illustrate the effect of doubling the synergist dosage while holding the mobam dosage constant at 0.20 mg/fly, i.e. the effect of varying the synergist-insecticide ratio.

TABLE X

| Mobam dose: | 0 | 0.20 | 0.20 | 0.10 | 0.10 | 0.05 | 0.05 | 0.20 | 0.20 |
| --- | --- | --- | --- | --- | --- | --- | --- | --- | --- |
| Synergist dose: | 1 | 0 | 1 | 0 | 0.50 | 0 | 0.25 | 0.50 | 0.25 |
| Synergist Compound No. | | | | | | | | | |
| I-B | 0 | 6 | 73 | — | 0 | — | 0 | 30 | 13 |
| I-D | 0 | 2 | 92 | 0 | 20 | 0 | 8 | — | — |
| I-F | 0 | 7 | 47 | — | — | — | — | — | — |

The effect of O-(2-propynyl) oximes with Dimetilan and with GS 13798 was obtained from tests on polyvalent resistant (CH strain) housefllies that had been chilled and to the dorsal region of which was applied an acetone solution of synergist and insecticide at a ratio of two to one. Duplicate tests were performed using four to five-day old female houseflies per test. After dosage, the flies were put in a plastic petri dish with cotton soaked in a sugar-water solution. The percent

TABLE XI

| Mobam dose: | 0 | 0 | 0.60 | 0.30 | 0.60 | 0.30 | 0.15 |
| --- | --- | --- | --- | --- | --- | --- | --- |
| Synergist dose: | 7.5 | 5.0 | 0 | 0 | 3.0 | 1.5 | 0.75 |
| Synergist Compound No. | | | | | | | |
| I-B | — | 0 | — | 0 | — | 40 | — |
| I-D | 0 | — | 4 | 0 | 100 | 95 | 19 |
| I-F | — | 0 | — | 0 | — | 38 | — |

EXAMPLE 6

Synergism of Insecticidal Carbamates By Benzyl 2-Propynyl Ethers.

The synergistic effect with carbyl and pyrolan of the synergist compounds II-A through II-H identified in Table II was determined by the jar-film assay technique of Example 5. The contact synergistic ratios are given in Table XII.

TABLE XII

| Compound No. | Contact Synergistic Ratio | |
|---|---|---|
| | Carbaryl | Pyrolan |
| II-A | 50 | 7 |
| II-B | 50 | 15 |
| II-C | 100 | 15 |
| II-D | 200 | 30 |
| II-E | 120 | 20 |
| II-F | 150 | 15 |
| II-G | 100 | 15 |
| II-H | 300 | 40 |

The effect of compounds II-C, II-D and II-E with Dimetilan and GS 13798 was determined, following the procedure of Example 5, from tests on polyvalent resistant (CH strain) houseflies. The percent kills after 24 hours are shown in Table XIII. These doses of insecticide used without synergist caused 10–40% mortality.

TABLE XIII

| | | Dimetilan | GS 13798 |
|---|---|---|---|
| Insecticide dose: | 0 | 2 | 1 |
| Synergist dose: | 10 | 4 | 2 |
| Synergist Compound No. | | | |
| II-C | 0 | 100 | 92 |
| II-D | 0 | 100 | 100 |
| II-E | 10 | 100 | 100 |

The synergistic effect of benzyl 2-propynyl ethers with mobam was determined from topical application tests on IN/WHO and Rutgers A strain houseflies, following the procedure of Example 5. The percent kills after 24 hours are shown in Table XIV for the IN/WHO strain and in Table XV for the Rutgers A strain.

TABLE XIV

| Mobam dose: | 0 | 0.20 | 0.20 | 0.10 | 0.10 | 0.05 | 0.05 |
|---|---|---|---|---|---|---|---|
| Synergist dose: | 1.0 | 0 | 1.0 | 0 | 0.50 | 0 | 0.25 |
| Synergist Compound No. | | | | | | | |
| II-C | — | 2 | 99 | 0 | 27 | 0 | 4 |
| II-D | 0 | 2 | 100 | 0 | 50 | 0 | 10 |
| II-E | 0 | 2 | 100 | 0 | 33 | 0 | 5 |
| II-H | 10 | 25 | 100 | | | | |
| II-I | 7 | 25 | 97 | | | | |
| II-J | 13 | 25 | 100 | | | | |
| II-K | 10 | 25 | 100 | | | | |
| II-L | 3 | 25 | 89 | | | | |
| II-M | 10 | 25 | 90 | | | | |
| II-N | — | 12 | 97 | | | | |
| II-O | 10 | 25 | 60 | | | | |

TABLE XV

| Mobam dose: | 0 | 0 | 0.60 | 0.40 | 0.60 | 0.40 | 0.30 | 0.30 | 0.15 | 0.15 |
|---|---|---|---|---|---|---|---|---|---|---|
| Synergist dose: | 7.5 | 5.0 | 0 | 0 | 3.0 | 2.0 | 0 | 1.5 | 0 | 0.75 |
| Synergist Compound No. | | | | | | | | | | |
| II-C | 0 | — | 4 | — | 67 | — | 0 | 20 | — | — |
| II-D | 0 | — | 4 | — | 92 | — | — | — | — | — |
| II-E | 0 | — | 4 | — | 99 | — | 0 | 70 | 0 | 17 |
| II-H | — | 7 | — | 7 | — | 100 | | | | |
| II-I | — | 3 | — | 7 | — | 37 | | | | |
| II-J | — | 0 | — | 7 | — | 70 | | | | |
| II-K | — | 0 | — | 7 | — | 97 | | | | |
| II-L | — | 0 | — | 7 | — | 52 | | | | |

The effects of varying the insecticide dose and the synergist-insecticide ratio are further illustrated, with synergist compounds II-D, II-E, II-F and Mobam insecticide, in Tables XVI, XVII and XVIII. Table XVI shows percent mortality of the subject IN/WHO houseflies 24 hours after topical application of Mobam, both with and without synergist compound II-D; Table XVII shows the mortality data using synergist compound II-E; and Table XVIII shows the mortality data using synergist compound II-F.

TABLE XVI

| Synergist/ Insecticide ratio: | Insecticide alone | 0.5/1 | 1/1 | 2/1 | 5/1 |
|---|---|---|---|---|---|
| Insecticide Dose | | | | | |
| 1.0 | 73 | 97 | 100 | 100 | 100 |
| 0.50 | 33 | 57 | 100 | 97 | 100 |
| 0.25 | 7 | 30 | 63 | 83 | 97 |
| 0.13 | 0 | 7 | 17 | — | 50 |

TABLE XVII

| Synergist/ Insecticide ratio: | Insecticide alone | 0.5/1 | 1/1 | 2/1 | 5/1 |
|---|---|---|---|---|---|
| Insecticide Dose | | | | | |
| 1.0 | 93 | 100 | 100 | 100 | 100 |
| 0.50 | 83 | 97 | 97 | 93 | 100 |
| 0.25 | 27 | 53 | 77 | 73 | 67 |
| 0.13 | — | 30 | 27 | 17 | 40 |

TABLE XVIII

| Synergist/ Insecticide ratio: | Insecticide alone | 0.5/1 | 1/1 | 2/1 | 5/1 |
|---|---|---|---|---|---|
| Insecticide Dose | | | | | |
| 1.0 | 93 | 100 | 93 | 93 | 100 |
| 0.50 | 83 | 70 | 83 | 80 | 97 |
| 0.25 | 27 | 33 | 57 | 27 | 73 |
| 0.13 | — | 3 | 10 | 0 | 23 |

The data in Table XVI illustrate that a dose of insecticide (1.0 μg/fly) which would not be considered to give adequate conquate control ($LD_{73}$) does give such control ($LD_{97}$) when used with 0.5μg of synergist. Furthermore when the applied dose consists of equal parts of Mobam and II-D, the dose of Mobam need only be 0.5μg to achieve $LD_{100}$.

The synergistic effect on IN/WHO flies of synergist compound II-K with Dimetilan, pyrolan, Baygon and HRS 1422 is illustrated by the 24 hour percent mortality data in Tables XIX, XX and XXI.

TABLE XIX

| Dimetilan Dose | Dimetilan Alone | Dimetilan With Five Parts II-K |
|---|---|---|
| 0.25 | 100 | — |
| 0.13 | 43 | 100 |
| 0.063 | 17 | 70 |
| 0.031 | 0 | 7 |

TABLE XX

| Pyrolan Dose | Pyrolan alone | Pyrolan With Five Parts II-K |
|---|---|---|
| 5.0 | 43 | — |
| 2.5 | 10 | — |
| 1.3 | 3 | — |
| 0.63 | 0 | — |
| 0.25 | — | 80 |
| 0.13 | — | 40 |
| 0.063 | — | 7 |

TABLE XXI

| Insecticide | Baygon alone | Baygon With Five Parts II-K | HRS 1422 | HRS 1422 With Five Parts II-K |
|---|---|---|---|---|
| 0.125 | 0 | 83 | 0 | 77 |

EXAMPLE 7

Synergism of Insecticidal Carbamates By N-(2-Propynyl) Indazoles.

The synergistic effect with carbaryl and pyrolan of synergist compounds III-A, III-B, III-C and III-D, identified in Table III, was determined by the jar-film assay technique of Example 5. The contact synergistic ratios are given in Table XXII.

TABLE XXII

| Compound No. | Contact Synergistic Ratio | |
|---|---|---|
| | Carbaryl | Pyrolan |
| III-A | 143 | 30 |
| III-B | 117 | 30 |
| III-C | 53 | 10 |
| III-D | 250 | 25 |

EXAMPLE 8

Synergism of Insecticidal Carbamates By (2-Propynyloxy) Alkyl Arenes.

The synergistic effect with carbaryl and pyrolan of synergist compounds IV-A and IV-B, identified in Table IV, was determined by the jar-film assay technique of Example 5. The contact synergistic ratios are given in Table XXIII.

TABLE XXIII

| Compound No. | Contact Synergistic Ratio | |
|---|---|---|
| | Carbaryl | Pyrolan |
| IV-A | 134 | 10 |
| IV-B | 50 | 10 |

The effect on IN/WHO flies of synergist compound IV-C, identified in Table IV, with mobam was determined by the topical application procedure of Example 5. The percent kills after 24 hours are shown in Table XXIV.

TABLE XXIV

| Mobam dose: | 0 | 0.20 | 0.20 | 0.20 | 0.20 |
|---|---|---|---|---|---|
| Synergist dose: | 1 | 0 | 1 | 0.50 | 0.25 |
| Synergist Compound No. | | | | | |
| IV-C | 0 | 9 | 64 | 60 | 39 |

EXAMPLE 9

Synergism of Insecticidal Organophosphorus Compounds By O-(2-Propynyl) Oximes.

The synergistic effect with Diazinon of compounds I-B, I-D, I-F, I-G, I-H and I-I, identified in Tables I and Ia, was determined from topical application tests on IN/WHO strain houseflies and on Rutgers A strain houseflies by the procedure of Example 5. The percent kills after 24 hours are shown in Table XXV for the IN/WHO strain and Table XXVI for the Rutgers A strain.

TABLE XXV

| Diazinon dose: | 0 | 0.02 | 0.03 | 0.02 | 0.03 |
|---|---|---|---|---|---|
| Synergist dose: | 1 | 0 | 0 | 0.10 | 0.15 |
| Synergist Compound No. | | | | | |
| I-B | 0 | — | 0 | — | 22 |
| I-D | 0 | — | 5 | — | 50 |
| I-F | 0 | — | 0 | — | 24 |
| I-G | 0 | 3 | — | 40 | — |
| I-H | 0 | 3 | — | 47 | — |

TABLE XXVI

| Diazinon dose: | 0 | 0 | 0 | 3.0 | 1.5 | 1.0 | 3.0 | 3.0 | 1.5 | 1.0 |
|---|---|---|---|---|---|---|---|---|---|---|
| Synergist dose: | 15 | 7.5 | 5 | 0 | 0 | 0 | 15 | 3.0 | 7.5 | 3.0 |
| Synergist Compound No. | | | | | | | | | | |
| I-B | — | — | 0 | 5 | — | 0 | — | 90 | — | 5 |
| I-D | — | 0 | — | — | 3 | — | — | — | 69 | — |
| I-F | — | — | 0 | 5 | — | 0 | — | 95 | — | 5 |
| I-G | 0 | 0 | — | 18 | 0 | — | 100 | — | 60 | — |
| I-H | 0 | 0 | — | 18 | 0 | — | 100 | — | 80 | — |
| I-I | 0 | 0 | — | 18 | 0 | — | 53 | — | 0 | — |

TABLE XXVII

| Diazinon dose: | 0 | 5 |
|---|---|---|
| Synergist dose: | 10 | 10 |
| Synergist Compound No. | | |
| I-A | 0 | 45 |
| I-D | 0 | 100 |
| I-E | 0 | 90 |
| I-G | 0 | 90 |
| I-I | 0 | 55 |

The synergistic effect with GS 13005 of compounds I-A, I-B, I-D, I-E, I-F, I-G and I-I was determined from topical application tests to IN/WHO strain, Rutgers A strain and polyvalent CH strain houseflies using the procedures of Example 5. The percent kills of the IN/WHO strain flies after 24 hours are shown in Table XXVIII; of the Rutgers A strain, in Table XXIX; and of the polyvalent CH strain, in Table XXX. The doses of insecticide alone to the CH strain files caused 10–40% mortality.

TABLE XXVIII

| GS 13005 dose: | 0 | 0.10 | 0.10 | 0.10 | 0.10 | 0.05 |
|---|---|---|---|---|---|---|
| Synergist dose: | 1 | 0 | 0.50 | 0.25 | 0.125 | 0.25 |
| Synergist Compound No. | | | | | | |
| I-B | 0 | 12 | 73 | 27 | 13 | 2 |
| I-F | 0 | 20 | 45 | — | — | — |

TABLE XXIX

| GS 13005 dose: | 0 | 1 | 1 |
|---|---|---|---|
| Synergist dose: | 5 | 0 | 5 |
| Synergist Compound No. | | | |
| I-B | 0 | 2 | 100 |
| I-F | 0 | 2 | 95 |

TABLE XXX

| GS 13005 dose: | 0 | 1 |
|---|---|---|
| Synergist dose: | 10 | 2 |
| Synergist Compound No. | | |
| I-A | 0 | 45 |
| I-D | 0 | 100 |
| I-F | 0 | 100 |
| I-G | 0 | 100 |

TABLE XXX-continued

| GS 13005 dose: | 0 | 1 |
|---|---|---|
| Synergist dose: | 10 | 2 |
| Synergist Compound No. | | |
| I-I | 0 | 47 |

EXAMPLE 10

Synergism of Insecticidal Organophosphorus Compounds By Benzyl 2-Propynyl Ethers.

The synergistic effect with Diazinon and GS 13005 of various of the benzyl 2-propynyl ethers identified in Tables II and IIa was determined by topical application tests on IN/WHO strain, and Rutgers A strain and polyvalent, resistant, CH strain houseflies using the procedures of Example 5. The percent kills after 24 hours of IN/WHO strain flies are shown in Table XXXI; of Rutgers A strain flies, in Table XXXII; and of CH strain flies, in Table XXXIII. The doses of insecticide alone to the CH strain flies causes 10–40% mortality.

TABLE XXXI

| | Diazinon | | | GS 13005 | | | | | |
|---|---|---|---|---|---|---|---|---|---|
| Insecticide dose: | 0 | 0.03 | 0.03 | 0 | 0.10 | 0.10 | 0.10 | 0.10 | 0.05 | 0.05 |
| Synergist dose: | 1 | 0 | 0.15 | 1 | 0 | 0.50 | 0.25 | 0.125 | 0 | 0.25 |
| Synergist Compound No. | | | | | | | | | | |
| II-C | 0 | 5 | 25 | — | — | — | — | — | — | — |
| II-D | 0 | 5 | 40 | — | — | — | — | — | — | — |
| II-E | 0 | 5 | 45 | — | — | — | — | — | — | — |
| II-H | — | — | — | 10 | 19 | 100 | — | — | — | — |
| II-I | — | — | — | 7 | 19 | 99 | — | — | — | — |
| II-J | — | — | — | 13 | 19 | 99 | — | — | — | — |
| II-K | — | — | — | 10 | 19 | 100 | — | — | — | — |
| II-L | — | — | — | 3 | 19 | 97 | — | — | — | — |
| II-M | — | — | — | 10 | 19 | 79 | — | — | — | — |
| II-N | — | — | — | — | 7 | 84 | — | — | — | — |
| II-O | — | — | — | 10 | 19 | 90 | — | — | — | — |
| II-P | 0 | 0 | 30 | 0 | 16 | 96 | 85 | 69 | 0 | 10 |
| II-Q | — | — | — | 0 | 16 | 90 | 67 | 43 | 0 | 25 |
| II-R | 0 | 0 | 22 | 0 | 12 | 68 | 65 | 49 | — | — |

TABLE XXXII

| GS 13005 dose: | 0 | 1.0 | 1.0 |
|---|---|---|---|
| Synergist dose: | 5.0 | 0 | 5.0 |
| Synergist Compound No. | | | |
| II-H | 7 | 13 | 100 |
| II-I | 3 | 13 | 83 |
| II-J | 0 | 13 | 100 |
| II-K | 0 | 13 | 100 |
| II-L | 0 | 13 | 83 |
| II-M | 0 | 13 | 63 |
| II-N | — | 2 | 60 |
| II-O | 3 | 13 | 47 |
| II-P | 0 | 3 | 92 |
| II-Q | 0 | 3 | 100 |
| II-R | 0 | 2 | 55 |

TABLE XXXIII

| | | Diazinon | GS 13005 |
|---|---|---|---|
| Insecticide dose: | 0 | 5 | 1 |
| Synergist dose: | 10 | 10 | 2 |
| Synergist Compound No. | | | |
| II-C | 0 | 95 | 75 |
| II-D | 0 | 60 | 95 |

TABLE XXXIII-continued

| Insecticide dose: | 0 | Diazinon 5 | GS 13005 1 |
|---|---|---|---|
| Synergist dose: | 10 | 10 | 2 |
| Synergist Compound No. | | | |
| II-E | 10 | 65 | 100 |

The synergist effect on IN/WHO flies of synergist compound II-K with Gardona and Bidrin is illustrated by the 24 hour percent mortality data in Tables XXXIV and XXXV.

TABLE XXXIV

| Gardona Dose | Gardona Alone | Gardona With Five Parts II-K |
|---|---|---|
| 0.125 | 100 | — |
| 0.063 | 73 | 100 |
| 0.031 | 13 | 63 |

TABLE XXXV

| Bidrin Dose | Bidrin Alone | Bidrin With Five Parts II-K |
|---|---|---|
| 0.13 | 0 | 57 |
| 0.063 | 0 | 0 |

EXAMPLE 11

Synergism of Insecticidal Organophosphorus Compounds By (2-Propynyloxy) alkyl Arenes.

The synergistic effect on IN/WHO strain flies and Rutgers A strain flies of compound IV-C with GS 13005 and with Diazinon was determined by the topical application procedure of Example 5. The percent kills of IN/WHO strain flies after 24 hours are shown in Tables XXXVI and XXXVII; the percent kills of Rutgers A strain flies are shown in Tables XXXVIII and XXXIX.

TABLE XXXVI

| GS 13005 dose: | 0 | 0.10 | 0.10 | 0.10 | 0.10 | 0.05 | 0.05 |
|---|---|---|---|---|---|---|---|
| Synergist dose: | 1 | 0 | 0.50 | 0.25 | 0.125 | 0 | 0.25 |
| Synergist IV-C | 0 | 10 | 89 | 75 | 63 | 0 | 9 |

TABLE XXXVII

| Diazinon dose: | 0 | 0.03 | 0.03 |
|---|---|---|---|
| Synergist dose: | 1 | 0 | 0.15 |
| Synergist IV-C | 0 | 0 | 29 |

TABLE XXXVIII

| GS 13005 dose: | 0 | 1.0 | 1.0 |
|---|---|---|---|
| Synergist dose: | 5 | 0 | 5.0 |
| Synergist IV-C | 0 | 3 | 95 |

TABLE XXXIX

| Diazinon dose: | 0 | 3.0 | 3.0 |
|---|---|---|---|
| Synergist dose: | 5 | 0 | 3.0 |
| Synergist IV-C | 0 | 5 | 19 |

EXAMPLE 12

Synergism of Mobam and GS 13005 In German Male Cockroaches.

The synergistic effect with mobam of synergist compounds I-B, II-H, II-K and IV-C is further illustrated by the 24 hour mortality data of German male cockroaches (Blatella Germanicus) shown in Table XXXX. The synergists and insecticide were diluted in acetone and applied in small droplets to the thorax of the insect. These doses of synergist alone gave zero percent insect mortality.

TABLE XXXX

| Mobam dose: | 0.12 | 0.12 | 0.16 | 0.16 |
|---|---|---|---|---|
| Synergist dose: | 0 | 0.60[a] | 0 | 0.80 |
| Synergist Compound No. | | | | |
| I-B | 10 | 80 | 30 | 50 |
| II-H | 10 | 90 | — | — |
| II-K | 10 | 100 | — | — |
| IV-C | 10 | 60 | 30 | 40 |
| Control[b] | — | 7 | — | 0 |
| Control[c] | — | 0 | — | 0 |

[a]Pretreated with synergist two hours before applying insecticide.
[b]Treated with acetone at time of treatment with synergist and also at time of treatment with insecticide.
[c]Untreated.

The synergistic effect with GS 13005 of compounds I-B, II-H, II-K, II-P, II-Q, II-R and IV-C is illustrated by the 24 hour mortality of German male cockroaches shown in Table XXXXI. These doses of synergist alone caused zero percent insect mortality.

TABLE XXXXI

| GS 13005 dose: | 0.08 | 0.08 | 0.08 |
|---|---|---|---|
| Synergist dose: | 0 | 4.0 | 0.40[a] |
| Synergist Compound No. | | | |
| I-B | 23 | 40 | 95 |
| II-H | 15 | — | 100 |
| II-K | 15 | — | 100 |
| II-P | 23 | 60 | 90 |
| II-Q | 10 | — | 95 |
| II-R | 10 | — | 100 |
| IV-C | 23 | 30 | 90 |
| Control[b] | 0 | 10 | 0 |
| Control[c] | 0 | 0 | 5 |

[a]Pretreated with synergist two hours before applying insecticide.
[b]Treated with acetone at time of treatment with synergist and also at time of treatment with insecticide.
[c]Untreated.

EXAMPLE 13

Synergism of Pyrethrum

The synergistic effect with pyrethrum of various synergist compounds was determined by topical application tests on polyvalent, resistant CH strain houseflies following the procedure of Example 5. The percent kills after 24 hours are reported in Table XXXXII. Application of the insecticide alone caused 10–40% mortality.

TABLE XXXXII

| Pyrethrum dose: | 0 | 2 |
|---|---|---|
| Synergist dose: | 10 | 4 |
| Synergist Compound No. | | |
| I-A | 0 | 15 |
| I-D | 0 | 67 |
| I-F | 0 | 35 |
| I-G | 0 | 47 |
| I-I | 0 | 52 |
| II-C | 0 | 50 |
| II-D | 0 | 30 |
| II-E | 10 | 78 |

The average percent knockdown of CH strain flies, as a function of time, resulting from spray application of pyrethrum, alone and with synergists, are given in Table XXXXIII. Duplicate tests were performed using 50 CH strain houseflies per test. Test solutions of 100 mg and 200mg of pyrethrum per cc of acetone, 200 mg of synergist per cc of acetone, and a mixture of 100 mg of pyrethrum and 100 mg of synergist per cc of acetone were prepared. The fifty CH strain houseflies were put in a 40 liter spray chamber and 1 cc of the test solution was sprayed into the test chamber with a spray pistol. The synergists alone at 200 mg/cc caused no knockdown.

EXAMPLE 14

Extension of Sleeping Time of Barbiturate and Non-Barbiturate Depressant Drugs by Synergists.

The effect of various synergist compounds on sleeping time of sodium secobarbital [Secobarbital] and of 3,3-diethyl-5-methyl-2,4-dioxypiperidine [Noludar] was determined by administering the drug, with and without synergist, to approximately 38-day old male mice weighing from 25 to 30 grams. Synergists were administered in each of two doses, 74.0 mg/kg (dilution being 2.0 mg/0.1 ml corn oil), and 110.0 mg/kg (dilution 3.0 mg/0.1 ml oil). Secobarbital was administered at a dose of 37.0 mg/kg (dilution 1.0 mg/0.1 ml water). Noludar was administered at a dose of 110.0 mg/kg (dilution 3.0 mg/0.1 ml water). The synergist was administered one hour prior to administration of the Secobarbital or Noludar. Secobarbital and Noludar sleeping times were obtained for both the control (drug only) and the treated (synergist plus drug) mice by noting the time lapse between the administration of the drug and the recovery of the righting reflex, i.e. when the animal regains conciousness and can walk up and inclined wooden tray with coordination. The relative sleeping time (R.S.) was noted. The R.S. is the extended sleeping time in the treated mice (synergist plus

TABLE XXXXIII

| Synergist No. | Dose (Mg/cc) Pyrethrum | Synergist | 5 | 10 | 15 | 20 | Minutes 25 | 30 | 40 | 50 | 60 |
|---|---|---|---|---|---|---|---|---|---|---|---|
| — | 100 | 0 | 3 | 6 | 14 | 25 | 32 | 37 | 58 | 62 | 62 |
| — | 200 | 0 | 3 | 27 | 44 | 60 | 60 | 64 | 82 | 86 | 87 |
| I-D | 100 | 100 | 6 | 15 | 26 | 39 | 52 | 60 | 86 | 87 | 88 |
| I-G | 100 | 100 | 7 | 12 | 31 | 36 | 59 | 66 | 89 | 93 | 94 |
| I-I | 100 | 100 | 4 | 7 | 19 | 29 | 40 | 49 | 57 | 86 | 92 |
| II-E | 100 | 100 | 5 | 9 | 17 | 44 | 55 | 59 | 77 | 93 | 95 |

The selectivity of the synergist compounds of this invention is illustrated by the results of sleeping-time extension tests and of acute toxicity tests on Swiss albino white male mice.

drug) divided by the sleeping time in the control mice (drug only). The mean sleeping time for the treated mice and the R.S. are shown on Table XXXXIV for various synergist compounds.

TABLE XXXXIV

| | Secobarbital (37 mg/K) | | | | Noludar (110 mg/K) | |
|---|---|---|---|---|---|---|
| | Synergist (110 mg/K) | | Synergist (74 mg/K) | | Synergist (110 mg/K) | |
| Synergist Compound No. | Mean Sleeping Time (Min.) | Relative Sleeping Time | Mean Sleeping Time (Min.) | Relative Sleeping Time | Mean Sleeping Time (Min.) | Relative Sleeping Time |
| I-B | 106 | 1.7 | 54 | 1.5 | 70 | 2.4 |
| I-C | 108 | 1.8 | 30 | 1.1 | 34 | 1.0 |
| I-D | 56 | 1.7 | 62 | 1.9 | 58 | 1.5 |
| I-F | 70 | 2.2 | 32 | 1.1 | 55 | 1.4 |
| I-G | 55 | 1.7 | 27 | 1.0 | 48 | 1.2 |
| I-I | 102 | 1.7 | 31 | 1.1 | 62 | 2.1 |
| II-C | 33 | 1.0 | — | — | 50 | 1.3 |
| II-D | 60 | 1.2 | — | — | 46 | 1.0 |
| II-E | 44 | 1.4 | — | — | 45 | 1.1 |
| II-F | 46 | 1.0 | — | — | 38 | 1.3 |
| II-H | 51 | 2.1 | 44 | 1.4 | 68 | 2.2 |
| II-I | 32 | 1.3 | 31 | 1.2 | 56 | 1.8 |
| II-J | 30 | 1.4 | 27 | 1.0 | 70 | 2.2 |
| II-K | 44 | 2 | 48 | 1.5 | 75 | 2.4 |
| II-L | 42 | 1.8 | 31 | 1.0 | 56 | 1.8 |
| II-M | 47 | 2 | 29 | 1.0 | 47 | 2.1 |
| II-N | 39 | 1.7 | 20 | 1.0 | 58 | 1.9 |
| II-O | 26 | 1.1 | — | — | 52 | 2.4 |
| II-P | 46 | 1.0 | — | — | 44 | 1.5 |
| II-Q | 73 | 1.6 | 30 | 1.1 | 41 | 2.1 |
| II-R | 96 | 1.6 | 35 | 1.2 | 49 | 1.7 |
| III-A | 50 | 1.1 | — | — | 32 | 1.0 |
| III-B | 6 | 1.3 | — | — | 46 | 1.0 |
| III-D | 55 | 1.2 | — | — | 45 | 1.5 |
| IV-A | — | — | 56 | 2.3 | 78 | 2.7 |
| IV-C | — | — | 112 | 4.7 | 74 | 2.5 |

TABLE XXXXIV-continued

| Synergist Compound No. | Secobarbital (37 mg/K) | | | | Noludar (110 mg/K) | |
|---|---|---|---|---|---|---|
| | Synergist (110 mg/K) | | Synergist (74 mg/K) | | Synergist (110 mg/K) | |
| | Mean Sleeping Time (Min.) | Relative Sleeping Time | Mean Sleeping Time (Min.) | Relative Sleeping Time | Mean Sleeping Time (Min.) | Relative Sleeping Time |
| Sesoxane | — | 8.3 | — | 6.1 | — | 3.1 |

EXAMPLE 15

Synergism of Acute Toxicity of Dimetilan, GS 13005, Secobarbital and Methadone.

To determine the acute toxicity of dimetilan alone, eight dosage levels of Dimetilan, ranging from 4 to 32 mg per kg wer applied to eight, Swiss, albino, white, male mice per dosage level. The mice weighed approximately 23 to 27 grams and were five to size weeks old. The number of mice dead 48 hours after administration of the Dimetilan (lethality) are shown in Table XXXXV. The Dimetilan was administered intraperitoneally in 0.1 ml of corn oil one hour after the administration of the same dose of corn oil alone.

TABLE XXXXV

| Dimetilan Dose (Mg/kg) | Lethality |
|---|---|
| 4.0 | 0 |
| 8.0 | 0 |
| 12.0 | 1 |
| 16.0 | 3 |
| 20.0 | 4 |
| 24.0 | 7 |
| 28.0 | 8 |
| 32.0 | 8 |

A dose level of 8 mg/kg of Dimetilan was utilized in the tests of synergism of acute toxicity as being the dose level just below that at which Dimetilan alone showed lethality to the mice.

To determine the acute toxicity of the synergist alone, various synergists were administered intraperitoneally at a dose of 1000 mg/kg to each of a group of eight mice. The number of animals dead at the end of 72 hours is reported in the left hand column of Table XXXXVI.

The synergism of the acute toxicity of Dimetilan by various synergists was determined by tests on Swiss albino, white male mice aged 5 to 6 weeks and weighing 23 to 27 grams. The synergists and insecticides were dissolved in corn oil and the drugs were dissolved in distilled water. All compounds were administered intraperitoneally by injection in the lower quadrent of the abdomen. The synergist was administered in 0.1 ml of corn oil 1 hour prior to administration of the insecticide. Eight mice were treated, per dosage, with each synergist. The mice were watched for a minimum of 6 hours while held in a glass jar with bedding individually after intraperitoneal injection of the test solutions. Lethality was noted, the animals were weighed and transferred in cages, and food and water were supplied. Control mice were given 0.1 ml of corn oil at the time of administration of the synergist to the test mice and 0.1 ml corn oil plus Dimetilan at the time of administration of the insecticide to the test mice. The number of mice dead at the end of 48 hours is reported in Table XXXXVI.

TABLE XXXXVI

| Dimetilan dose (Mg/kg): | 0 | 8 | 8 |
|---|---|---|---|
| Synergist dose (Mg/kg): | 1000 | 240 | 80 |
| Synergist Compound No. | | | |
| I-B | — | 6 | 1 |
| I-C | — | 0 | — |
| I-D | — | 6 | 1 |
| I-F | — | 4 | 0 |
| I-G | — | 0 | — |
| I-I | — | 3 | 0 |
| II-C | — | 0 | — |
| II-D | 0 | 0 | — |
| II-E | — | 0 | — |
| II-F | — | 0 | — |
| II-H | 0 | 6 | 0 |
| II-I | — | 3 | 0 |
| II-J | — | 4 | 0 |
| II-K | 1 | 6 | 0 |
| II-L | — | 5 | 0 |
| II-M | — | 3 | 0 |
| II-N | — | 4 | 0 |
| II-O | — | 2 | 0 |
| II-P | 2 | 0 | — |
| II-Q | 7 | 1 | — |
| II-R | — | 2 | 0 |
| III-A | — | 0 | — |
| III-B | — | 0 | — |
| III-D | — | 1 | — |
| IV-A | — | 7 | 4 |
| IV-C | — | 7 | 5 |
| Sesoxane | 1 | 8 | 8 |
| Control (0.1 ml oil) | 0 | 0 | 0 |

By the same procedure, the synergism of acute toxicity of GS 13005, Secobarbital and 6-dimethylamino-4,4-diphenyl-3-heptanone [Methadone] was determined. The mice lethality data are shown in Table XXXXVII.

TABLE XXXXVII

| | GS 13005 | Secobarbital | Methadone |
|---|---|---|---|
| Insecticide or Drug Dose (Mg/kg): | 71 | 90 | 32 |
| Synergist Dose (Mg/kg): | 213 | 215 | 215 |
| Synergist Compound No. | | | |
| II-D | 3 | 1 | 2 |
| II-H | 7 | 0 | 4 |
| II-J | 6 | 0 | 3 |
| II-K | 3 | 1 | 2 |
| II-P | 6 | 0 | 0 |
| II-Q | 6 | — | — |
| Sesoxane | 0 | 6 | 5 |
| Control | 5[a] | 0[b] | 2[c] |

[a]GS 13005 (71 mg/kg) in 0.1 ml corn oil.
[b]Secobarbital (90 mg/kg) in 0.1 ml corn oil.
[c]Methadone (32 mg/kg) in 0.1 ml corn oil.

I claim:
1. A propynyloxy alkyl arene compound represented by the formula

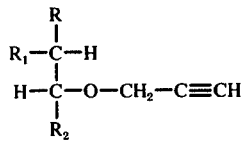

wherein R represents hydrogen or alkyl of not more than three carbon atoms, $R_1$ represents nitro, and $R_2$ represents an aromatic hydrocarbon selected from the class consisting of naphthyl and groups having the structural formula

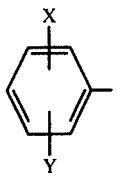

wherein X and Y represent hydrogen, nitro or halogen other than iodine.

2. A compound as claimed in claim 1 wherein R is methyl and $R_2$ is chlorophenyl.

3. A compound as claimed in claim 1 wherein R is methyl and $R_2$ is 4-chlorophenyl.

4. A compound as claimed in claim 1 wherein R is methyl and $R_2$ is 2,4-dichlorophenyl.

5. A compound as claimed in claim 1 wherein R is methyl and $R_2$ is naphthyl.

6. A compound as claimed in claim 1 wherein R is methyl.

7. A compound as claimed in claim 1 wherein R is methyl and $R_2$ is α-naphthyl.

* * * * *